US008247198B2

(12) United States Patent
Gorke et al.

(10) Patent No.: US 8,247,198 B2
(45) Date of Patent: Aug. 21, 2012

(54) ENZYMATIC PROCESSING IN DEEP EUTECTIC SOLVENTS

(75) Inventors: Johnathan T. Gorke, St. Paul, MN (US); Romas J. Kazlauskas, Falcon Heights, MN (US); Friedrich Srienc, Lake Elmo, MN (US)

(73) Assignee: Friedrich Srienc, St. Paul, MN (US)

( * ) Notice: Subject to any disclaimer, the term of this patent is extended or adjusted under 35 U.S.C. 154(b) by 868 days.

(21) Appl. No.: 12/284,466

(22) Filed: Sep. 22, 2008

(65) Prior Publication Data

US 2009/0117628 A1    May 7, 2009

Related U.S. Application Data

(60) Provisional application No. 60/994,783, filed on Sep. 21, 2007.

(51) Int. Cl.
- *C12P 13/02* (2006.01)
- *C12P 7/62* (2006.01)
- *C12N 9/10* (2006.01)
- *C12N 9/14* (2006.01)
- *C12N 9/18* (2006.01)
- *C12N 9/88* (2006.01)
- *C12N 9/48* (2006.01)
- *C12N 9/78* (2006.01)

(52) U.S. Cl. ........ 435/129; 435/135; 435/193; 435/196; 435/212; 435/227; 435/232

(58) Field of Classification Search ............. 435/129, 435/135, 193, 196, 212, 227, 232
See application file for complete search history.

(56) References Cited

U.S. PATENT DOCUMENTS

| | | | |
|---|---|---|---|
| 4,791,168 | A | 12/1988 | Salatin et al. |
| 4,794,147 | A | 12/1988 | Savino et al. |
| 5,147,791 | A | 9/1992 | Morrow et al. |
| 5,270,421 | A | 12/1993 | Dordick et al. |
| 5,474,915 | A | 12/1995 | Dordick et al. |
| 5,631,343 | A | 5/1997 | Binns et al. |
| 5,981,240 | A | 11/1999 | Akkara et al. |
| 6,677,427 | B1 | 1/2004 | Cheng et al. |
| 2004/0019178 | A1 | 1/2004 | Gross et al. |

OTHER PUBLICATIONS

Zhao et al., "Use of ionic liquids as green solvents for extractions", J. Chem. Technol. Biotechnol., 80 (10):1089-1096 (2005).
Zhu et al., "Supported choline chloride/urea as a heterogeneous catalyst for chemical fixation of carbon dioxide to cyclic carbonates", Green Chem., 9(1):169-172 (2007).
Abbott et al., "Preparation of novel, moisture-stable, Lewis-acidic ionic liquids containing quaternary ammonium salts with functional side chains", Chem. Commun., 19:2010-2011 (2001).
Abbott et al., "Novel solvent properties of choline chloride/urea mixtures", Chem. Commun., 1:70-71 (2003).
Abbott et al., "Eutectic-Based Ionic Liquids with Metal-Containing Anions and Cations", Chem. Eur. J., 13 (22):6495-6501(2007).
Abbott et al., "Design of improved deep eutectic solvents using hole theory", ChemPhysChem., 7(4):803-806 (Apr. 10, 2006).
Abbott et al., "Cationic functionalisation of cellulose using a choline based ionic liquid analogue", Green Chem., 8:784-786 (2006).
Abbott et al., "Extraction of glycerol from biodiesel into a eutectic based ionic liquid", Green Chem., 9:868-872 (2007).
Abbott et al., "Deep Eutectic Solvents Formed between Choline chloride and Carboxylic Acids: Versatile Alternatives to Ionic Liquids", J. Am. Chem. Soc., 126:9142-9147 (2004).
Abbott et al., "Electrodeposition of Zinc Tin Alloys from Deep Eutectic Solvents Based on Choline Chloride", J. Electroanal. Chem., 599:288-294 (2007).
Abbott et al., "Application of Hole Theory to Define Ionic Liquids by their Transport Properties", Phys. Chem. B, 111(18):4910-4913 (2007).
Abbott et al., "Electropolishing of stainless steels in a choline chloride based ionic liquid: an electrochemical study with surface characterisation using SEM and atomic force microscopy", Phys. Chem. Chem. Phys., 8:4214-4221 (2006).
Abbott et al., "Electroless deposition of metallic silver from a choline chloride-based ionic liquid: a study using acoustic impedance spectroscopy, SEM and atomic force microscopy", Phys. Chem. Chem. Phys., 9:3735-3743 (2007).
Abbott et al., "Sustained electroless deposition of metallic silver from a choline chloride-based ionic liquid", Surf. Coat. Technol., 202:2033-2039 (2008).
Biswas et al., "Ionic liquids as solvents for biopolymers: Acylation of starch and zein protein", Carbohyd. Polym., 66 (4):546-550 (2006).
Burrell et al., "The large scale synthesis of pure imidazolium and pyrrolidinium ionic liquids", Green Chem., 9:449-454 (2007).
Cheeseman et al., "Structure of an aryl esterase from *Pseudomonas fluorescens*", Acta Cryst., D60:1237-1243 (2004).
Dong et al., "Estimation on the Individual Hydrogen-Bond Strength in Molecules with Multiple Hydrogen Bonds", J. Phys. Chem. A, 111(15):2941-2945 (2007).
Genzel et al., "Microbiological transformations. Part 48: Enantioselective biohydrolysis of 2-,3- and 4-pyridyloxirane at high substrate concentration using the Agrobacterium radiobacter AD1 epoxide hydrolase and its Tyr215Phe mutant", Tetrahedron, 57(14):2775-2779 (2001).
Gordon, "New developments in catalysis using ionic liquids" Appl. Catal. A. Gen., 222(1-2):101-117 (Dec. 20, 2001). Gorke et al., "Hydrolase-catalyzed biotransformations in deep eutectic solvents", Chem. Commun., 10:1235-1237 (2008).
Gorke et al.,"Enzymatic synthesis of poly(hydroxyalkanoates) in ionic liquids", J. Biotechnol., 132(3):306-313 (2007).
Gurka et al., "Studies of hydrogen-bonded complex formation with p-fluorophenol. IV. Fluorine nuclear magnetic resonance method", J. Am. Chem. Soc., 91(17):4794-4801 (Aug. 13, 1969).
Jain et al., "Chemical and biochemical transformations in ionic liquids", Tetrahedron, 61(5):1015-1060 (2005).

(Continued)

Primary Examiner — Herbert J Lilling
(74) Attorney, Agent, or Firm — Dardi & Herbert, PLLC; Curtis B. Herbert

(57) ABSTRACT

It has surprisingly been discovered that it is possible to use enzymes in deep eutectic solvents (DES). DES's are mixtures of a nitrogen salt or a metal salt and a strong hydrogen bond donor that can be mixed in proportions that form a eutectic point.

25 Claims, 3 Drawing Sheets

OTHER PUBLICATIONS

Jastorff et al., "How hazardous are ionic liquids? Structure-activity relationships and biological testing as important elements for sustainability evaluation" J Green Chem., 5:136-142 (2003).

Joris et al., "Effects of polar aprotic solvents on linear free-energy relations in hydrogen-bonded complex formation", J. Am. Chem. Soc., 94(10): 3438-3442 (May 17, 1972).

Kragl et al., "Enzyme catalysis in ionic liquids", Curr. Opin. Biotechnol., 13(6):565-571 (Dec. 2002).

Kumar et al., "High-affinity salicylic acid-binding protein 2 is required for plant innate immunity and has salicylic acid-stimulated lipase activity". PNAS, 100(26):16101-16106 (Dec. 23, 2003).

Lamarche et al., "Theoretical Prediction of the Hydrogen-Bond Basicity pKHB", Chem. Eur. J. 8(2):457-466 (2002).

Lau et al., "Lipase-Catalyzed Reactions in Ionic Liquids", Org. Lett., 2(26):4189-4191 (2000).

Lee et al., "Adverse effect of chloride impurities on lipase-catalyzed transesterifications in ionic liquids" Biotechnol. Lett., 28(17):1335-1339 (2006).

Lozano et al., "Over-stabilization of *Candida antarctica* lipase B by ionic liquids", Biotechnol. Lett., 23:1529-1533 (2001).

Nkuku et al., "Electrochemistry in Deep Eutectic Solvents", J. Phys. Chem. B, 111(46):13271-13277 (2007).

Park et al., "Biocatalysis in ionic liquids—advantages beyond green technology", Curr. Opin. Biotechnol., 14 (4):432-437 (2003).

Park et al., "Improved preparation and use of room-temperature ionic liquids in lipase-catalyzed enantio- and regioselective acylations", J. Org. Chem., 66(25): 8395-8401 (Dec. 14, 2001).

Parnham et al., "Ionothermal Materials Synthesis Using Unstable Deep-Eutectic Solvents as Template-Delivery Agents", Angew. Chem. Int. Ed., 45(30):4962-4966 (2006).

Ranke et al., "Biological effects of imidazolium ionic liquids with varying chain lengths in acute *Vibrio fischeri* and WST-1 cell viability assays", Ecotoxicol. Environ. Saf., 58(3):396-404 (2004).

Reichardt, "Solvatochromic Dyes as Solvent Polarity Indicators", Chem. Rev., 94(8): 2319-2358 (1994).

Reichardt, "Polarity of ionic liquids determined empirically by means of solvatochromic pyridinium N-phenolate betaine dyes", Green Chem., 7:339-351 (2005).

Rink et al., "Kinetic Mechanism of the Enantioselective Conversion of Styrene Oxide by Epoxide Hydrolase from *Agrobacterium radiobacter* AD1", Biochemistry, 37:18119-18127 (1998).

Rui et al., "Protein Engineering of Epoxide Hydrolase from *Agrobacterium radiobacter* AD1 for Enhanced Activity and Enantioselective Production of (R)-1-Phenylethane-1,2-Diol", Appl. Env. Microbiol., 71(7):3995-4003 (Jul. 2005).

Seddon et al., "Influence of chloride, water, and organic solvents on the physical properties of ionic liquids", Pure Appl. Chem., 72(12):2275-2287 (2000).

Sheldon et al., "Biocatalysis in ionic liquids", Green Chem., 4:147-151 (2002).

Spelberg et al., "Enantioselectivity of a recombinant epoxide hydrolase from *Agrobacterium radiobacter*", Tetrahedron Asymm., 9(3):459-466 (1998).

Stolte et al., "Anion effects on the cytotoxicity of ionic liquids", Green Chem., 8: 621-629 (2006).

Trodler et al., "Modeling structure and flexibility of *Candida antarctica* lipase B in organic solvents", BMC Structural Biology, 8:9 (Feb. 6, 2008).

van Rantwijk, "Biocatalysis in Ionic Liquid", Chem. Rev., 107:2757-2785 (2007).

Visser et al., "Traditional Extractants in Nontraditional Solvents: Groups 1 and 2 Extraction by Crown Ethers in Room-Temperature Ionic Liquids", Ind. Eng. Chem. Res, 39:3596-3604 (2000).

Wasserscheid et al., "Ionic Liquids—New Solutions for Transition Metal Catalysis", Angew. Chem. Int. Ed., 39(21):3772-3789 (Nov. 3, 2000).

Wasserscheid et al., Ionic Liquids in Synthesis, 2003, Wiley-VCH.

Welton, "Room-Temperature Ionic Liquids. Solvents for Synthesis and Catalysis", Chem. Rev., 99(8):2071-2084 (1999).

Zhao et al., "Applications of Ionic Liquids in Organic Synthesis", Aldrichim. Acta, 35(3):75-83 (2002).

Ammonium Salts choline bromide (ChBr)　　choline chloride (ChCl)　　acetylcholine chloride (AcChCl)

tetrabutylammonium chloride (Bu4NCl)　　triethylbenzylammonium chloride (Et3BzNCl)

Hydrogen Bond Donors

D-glucose (Glc)　　D-xylose (Xyl)　　D-arabinose (D-Ara)　　L-arabinose (L-Ara)

urea (U)　　formamide (F)　　glycerol (Gly)

ENZYMATIC PROCESSING IN DEEP EUTECTIC SOLVENTS

PRIORITY INFORMATION

This application claims priority to U.S. provisional patent application 60/994,783 filed on Sep. 21, 2007, hereby incorporated herein by reference.

STATEMENT OF GOVERNMENT SUPPORT

The United States government has certain rights in these inventions, with such rights deriving from a National Institutes of Health Biotechnology Training Grant that provided funding for certain portions of this work or support for certain individuals performing this work.

BACKGROUND

Enzymes are used for certain industrial applications. Enzymes are catalysts that speed up the rate of reaction between substances without themselves being consumed in the reaction occur except at temperatures so high they would threaten the well-being of the body. Enzymes are proteins. Changes in the pH or acidity of the environment can alter or completely inhibit an enzyme from catalyzing a reaction. This change in the pH can affect the polar and non-polar intramolecular attractive and repulsive forces and alter the shape of the enzyme and the active site such that the substrate molecule can no longer fit. Correcting pH or temperature imbalances will usually allow the enzyme to resume its original shape or conformation. Some substances, however, will break enzymatic bonds and disrupt its primary structure so that the enzyme is inhibited permanently. Many toxic substances break covalent bonds and cause the unraveling of the protein enzyme. Other toxic substances precipitate enzymes. Urea is commonly used to denature proteins.

SUMMARY

It has surprisingly been discovered that it is possible to use enzymes in deep eutectic solvents (DES). DES's are mixtures of a nitrogen salt or a metal salt and a strong hydrogen bond donor that can be mixed in proportions that form a eutectic point. These discoveries provide new and improved methods to make compounds, including new types of compounds. In fact, before these experiments were performed, DES appeared to be poor choice for enzyme-catalyzed reactions. DES's often have melting points below room temperature, low volatility, and high thermal stability and a strong hydrogen donor. Strong hydrogen bond donors, urea for instance, are expected to denature proteins so that use of an enzyme would not be expected to succeed. In addition, DES's contain halides, which inactivate proteins when present in ionic liquids such that inactivation of enzymes by the halides would also be expected in DES's. Surprisingly, however, it was found that many enzymes nevertheless retain activity in DES's.

Furthermore, the components within the DES's are surprisingly and significantly 20 to more than 600-fold less reactive for enzymes than expected. This lowered reactivity corresponds to 2-4 kcal/mol, similar to the energy associated with the formation of hydrogen bonds. Without being bound to a particular theory, it seems that the hydrogen bond network in DES's lowers the chemical potential of the components of DES's; this theory explains why the DES are suitable as solvents for such a wide range of reactions, and also explains the synergistic effect for the DES components used in combination as opposed to separate use, or use of a DES component in other solvent systems.

Accordingly, one embodiment of the invention is a method comprising enzymatic catalysis of a chemical reaction in a solution comprising a deep eutectic solvent. The reaction may be, e.g., transesterification, aminolysis, hydrolysis, perhydrolysis, and/or alcohol dehydrogenase activity. The reaction may be a polymerization reaction. The polymerization reaction may be catalyzed by an enzyme that is, e.g., a member of the group consisting of enzymes that catalyze transesterification, aminolysis, hydrolysis, perhydrolysis, alcohol dehydrogenation, oxidation-reduction, or dehydrogenation. The reaction may produce, e.g., an addition product or a condensation product. The polymerization reaction may produce, e.g., a polyester or a polyamide. An enzyme that catalyzes the enzyme-catalyzed chemical reaction may be, e.g., a member of the group consisting of transesterase, hydrolase, lipase, amidase, and dehydrogenase.

An embodiment of the invention is a composition for enzymatic reaction comprising a deep eutectic solvent and an enzyme. The composition may include one or more substrates for the enzyme. The concentrations of the enzymes and/or substrates may be adjusted to achieve an effective reaction, or a predetermined rate of reaction or reaction product concentration. The substrate may be, .e.g, a monomer or a macromer, with catalysis by the enzyme producing a polymer of the monomer or macromer.

In some embodiments of the method or composition the enzyme is a member of the group consisting of enzymes that catalyze transesterification, aminolysis, hydrolysis, perhydrolysis, alcohol dehydrogenation, oxidation-reduction, or dehydrogenation. Or the enzyme is a member of the group consisting of transesterase, hydrolase, lipase, amidase, and dehydrogenase.

The deep eutectic solvent may include, for instance, a first component that comprises a strong hydrogen bond donor and a second component that comprises a metal salt or a nitrogen salt. Cosolvents, e.g., organic or aqueous, may also be present in the deep eutectic solvent. For instance, the composition comprises, in certain embodiments, between about 10% and about 75% volume/volume of the deep eutectic solvent. The second component may comprise, e.g., a halide-containing salt of amines or metals, e.g., a transition metal. The first component may comprise a strong hydrogen bond donor that comprises a hydroxyl, amide, amine, aldehyde, or carboxylic acid. The first component may comprise, e.g., a strong hydrogen bond donor is a member of the group consisting of an organic acid, a urea, a thiourea, an amide, a hydroxyl group, a diol, a glycerol, a choline chloride, or a combination thereof. The deep eutectic solvent may comprise, e.g., a first component taken from the group consisting of choline chloride, ethylammonium chloride, choline bromide glycerol, terabutylammonium chloride, triethylbenzylammonium chloride, zinc chloride, and acetylcholine chloride, and a second component taken from the group consisting of acetamide ethylene glycol, glycerol, urea, malonic acid, formamide, arabinose, glucose, and xylose. In some embodiments, the deep eutectic solvent comprises a first component that comprises a strong hydrogen bond donor and a second component that comprises a metal salt or a nitrogen salt. The second component may comprise, e.g., a halide-containing salt of amines or metals. The second component may comprise, e.g., a halide-containing salt of a transition metal. The first component may comprise, e.g., a strong hydrogen bond donor that comprises a hydroxyl, amide, amine, aldehyde, or carboxylic acid. The first component may comprise, e.g., a strong hydrogen bond donor is a member of the group consisting of an organic acid, a urea, a thiourea, an amide, a hydroxyl group, a diol, a glycerol, and a choline chloride. In certain embodiments the deep eutectic solvent comprises a first component taken from the group consisting of choline chloride, ethylammonium chloride, choline bromide glycerol, terabutylammonium chloride, triethylbenzylammonium chloride, zinc chloride, and acetylcholine chloride, and a second component taken from the group consisting of acetamide ethylene glycol, glycerol, urea, malonic acid, formamide, arabinose, glucose, and xylose.

DETAILED DESCRIPTION OF PREFERRED EMBODIMENTS

Figure 1:
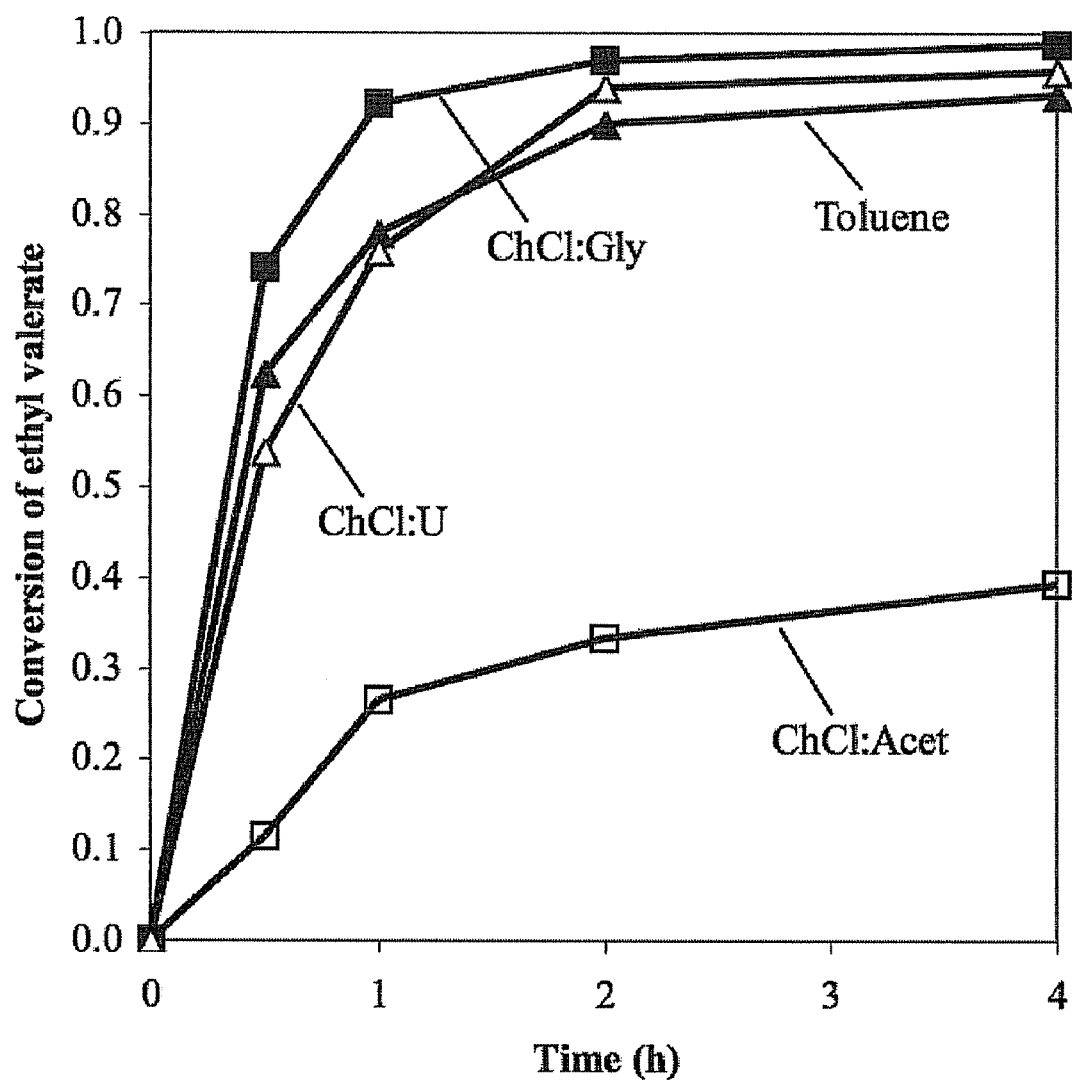
FIG. 1 is a demonstration of enzymatic aminolysis in DES, showing a plot of ethyl valerate (100 mM) with 1-butylamine (110 mM) at 60° C. with 10 mg ml$^{-1}$ iCALB; see Table 1 for abbreviations.

Enzymatic reactions may be performed in a DES. DES's are mixtures of an nitrogen salt or a metal salt and a hydrogen bond donor that can be mixed in proportions that form a eutectic point. The mixture of two or more solids has a melting point that depends on the composition, i.e. on the relative proportions of the constituent solids. A eutectic or eutectic mixture is a mixture at such proportions that the melting point is as low as possible, and that furthermore all the constituents crystallize at about the same time at this temperature from molten liquid solution. Such a simultaneous crystallization of an eutectic mixture is known as a eutectic reaction, the temperature at which it takes place is the eutectic temperature, and the composition and temperature at which it takes place is called the eutectic point.

DES's include a strong hydrogen bond donor, which is a reason that they are unlikely candidates for enzymatic catalysis because strong hydrogen bond donors, like urea, tend to denature proteins. For example, 10 M urea or 5 M choline chloride inactivates lipase B from *Candida antarctica* (70% or 25% loss in activity after 90 min at 60° C., respectively). DES also contain halides, which inactivate or inhibit proteins in other systems. In spite of these possible problems, however, it has been discovered that many hydrolases retain activity in DES.

The results set forth herein demonstrate that enzymatic transformations are possible in deep eutectic solvents (DES). Different lipases were active in eight of these solvents. In fact, *Candida antarctica* lipase B showed activity in every one of the DES's that were tested. This result shows that enzymes are not just active in one specific solvent but are generally active in DES. It is very likely that many DES across the whole class of DES solvents will allow enzymes to be active in them.

Further, many different types of enzymes and enzymatic reactions were tested across a variety of DES. These included transesterification, aminolysis, alcohol dehydrogenase activity, perhydrolysis activity, and hydrolysis activity. Enzymes included lipases, hydrolases, and esterases. In general, enzymes surprisingly had an activity for the DES components that was greatly reduced compared to activities for the components in other solvents. For instance, transesterification was highly specific for enzymatic reaction substrates even in the presence of DES components that were alcohols or glycerols. Moreover, polymerization reactions may also be performed in a DES.

Table 1 shows results of experiments using a lipase-catalyzed transesterification of ethyl valerate with 1-butanol:

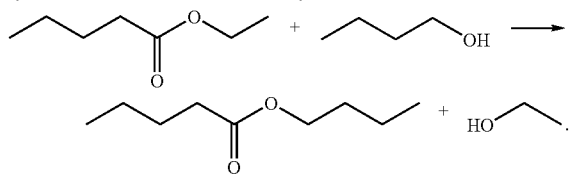

TABLE 1

| Percent conversion of ethyl valerate to butyl valerate at 60° C. | | | | | |
|---|---|---|---|---|---|
| Solvent (type) | iCALB | CALB | CALA | PCL | No Enzyme |
| ChCl:Acet (DES) | 23$^a$ | 96 | 0.5 | 0.0 | 0.0 |
| ChCl:EG (DES) | 11 (99)$^b$ | 32 (93)$^b$ | 3.0 | 0.2 | 0.0 |
| ChCl:Gly (DES) | 96 | 96 | 70 | 22 | 0.0 |
| ChCl:MA (DES) | 30 | 58 | 0.7 | 0.0 | 0.7 |
| ChCl:U (DES) | 93 | 99 | 1.6 | 0.8 | 0.0 |
| EAC:Acet (DES) | 63 | 92 | 2.7 | 0.0 | 0.0 |
| EAC:EG (DES) | 23 (54)$^b$ | 33 (79)$^b$ | 20 | 0.0 | 0.0 |
| EAC:Gly (DES) | 93 | 91 | 2.1 | 0.5 | 0.0 |
| Toluene (Organic) | 92 | 92 | 76 | 5.0 | 0.0 |

$^a$40 mM ethyl valerate, 400 mM-butanol, 10 mg ml-1 enzyme, 24 h.
$^b$Number in parentheses is the percent conversion including the side reaction with the ethylene glycol component of the deep eutectic solvent. No side reaction was detected in the other reactions.
Abbreviations of deep eutectic solvents - ChCl:Acet: choline chloride/acetamide; ChCl:EG: choline chloride/ethylene glycol; ChClGly: choline chloride/glycerol; ChCl:U: choline chloride/urea; ChCl:MA: choline chloride/malonic acid; EAC:Acet: ethylammonium chloride/acetamide; EAC:EG ethylammonium chloride/ethylene glycol; EAC:Gly: ethylammonium chloride/glycerol.

Referring to Table 1, the enzyme CALB (Roche CHIRAZYME L-2 (lyophilized *Candida antarctica* lipase B) and the enzyme immobilized form, iCALB (NOVOZYME 435 (*Candida antarctica* lipase B immobilized on acrylic resin)), catalyzed transesterification in all eight DES's tested and showed conversions comparable to that in toluene (organic solvent) for five of the DES's. The enzyme CALA (Roche CHIRAZYME L-5 (lyophilized *Candida antarctica* lipase A)) also showed activity in all eight DES's, but showed conversions comparable to toluene only in ChCl:Gly (76% vs. 70%). The enzyme Amano PS (lyophilized *Burkholderia* (formerly *Pseudomonas*) *cepacia* lipase)) (PCL) showed lower conversions that the other enzymes, but the conversion in one DES—ChCl:Gly—was higher that that in toluene (22 vs. 5%). The transesterification activity of CALB did not decrease in ChCl:U at 60° C. over 90 min, making it at least 20 to 35-fold more stable in the mixture than in aqueous solution of the components: 10 M urea or 5 M choline chloride. Example 1 provides further experimental details.

Some DES's shown in Table 1 contain an alcohol component, ethylene glycol, or glycerol, which compete with 1-butanol in transesterification. Indeed, ethylene glycol monoester was the major product for reaction in the two DES's containing ethylene glycol. For example, the CAL-B catalyzed reaction in EAC:EG showed 54% of starting material consumed resulting in 31% ethylene glycol monovalerate and 23% ethyl butyrate. This nearly equal amount of the two product esters is surprising because the concentration of ethylene glycol (10 M) was twenty-five times higher than the concentration of 1-butanol (400 mM). In a competition between ethylene glycol and 1-butanol in tert-butanol, 1-butanol reacted three times faster. Thus, ethylene glycol was 9-fold less reactive in transesterification when it was present as a component of a DES. DES can thus be effective solvents for reactions that consume substrates with a hydroxyl even when a DES component has a hydroxyl.

Even more surprising were the transesterification reactions in glycerol-containing DES's (8 M glycerol) which showed greater than 90% conversion and less than 0.5% glyceryl ester formation. In a competition between glycerol and 1-butanol in tert-butanol, 1-butanol reacted six times faster. Thus, glycerol was more than 600-fold less reactive in transesterification when it was present as a component of a DES.

The initial specific activity for the enzyme iCALB-catalyzed transesterification was comparable or higher in DES's as compared to typical ionic liquids, see Table 2. DES is not an ionic liquid and is unlike ionic liquids because the hydrogen bond donors are uncharged such that the nature of the chemical associations are highly distinct, ionic liquids are generally highly toxic compared to DES, and ionic liquids require different chemicals than DES. Previous work showed that iCALB had good transesterification activity in the ionic liquid 1-butyl-3-methylimidazolium bis(trifluoromethane) sulfonimide (BMIM [Tf$_2$N]) compared to other ionic liquids[9]. The ionic liquid 1-Butyl-3-methylimidazolium tetrafluoroborate (BMIM[BF$_4$]) is water miscible and preserves enzyme activity[10]. iCALB had the highest initial specific transesterification activity in the DES EAC:Gly (50 µmol ethyl valerate hr$^{-1}$ mg$^{-1}$), which was twice as high as for the ionic liquid BMIM[Tf$_2$N] (24 µmol hr$^{-1}$ mg$^{-1}$), seven times higher than the activity found in the ionic liquid BMIM[BF$_4$] (7 µmol hr$^{-1}$ mg$^{-1}$). The initial specific activity in toluene, and the DESs ChCl:Gly and ChCl:U ranged from 20 to 37 µmol hr$^{-1}$ mg$^{-1}$ and were comparable to that in the ionic liquid BMIM[Tf$_2$N].

TABLE 2

Initial specific activity of the enzyme iCALB after 15 minutes of reaction.

| Solvent (Type) | Tranesterification activity[a] | Aminolysis activity[a] |
|---|---|---|
| Toluene (Organic) | 37 (100%) | 46 (100%) |
| ChCl:Gly (DES) | 33 (89%) | 52 (113%) |
| ChCl:U (DES) | 20 (54%) | 22 (48%) |
| EAC:Gly (DES) | 50 (135%) | Not Determined[b] |
| BMIM[Tf2N] (Ionic Liquid) | 24 (65%) | 11 (24%) |
| BMIM[BF4] (Ionic Liquid) | 7 (19%) | 9 (19%) |

[a]µmol ethyl valerate hr$^{-1}$ mg solid$^{-1}$, activity relative to toluene in parentheses. iCALB contains ~10 wt % protein.
[b]Aminolysis with ethylamine from the DES was the dominant reaction.

The enzyme iCALB also catalyzed another model reaction in DES's: aminolysis of ethyl valerate with 1-butylamine, see also FIG. 1:

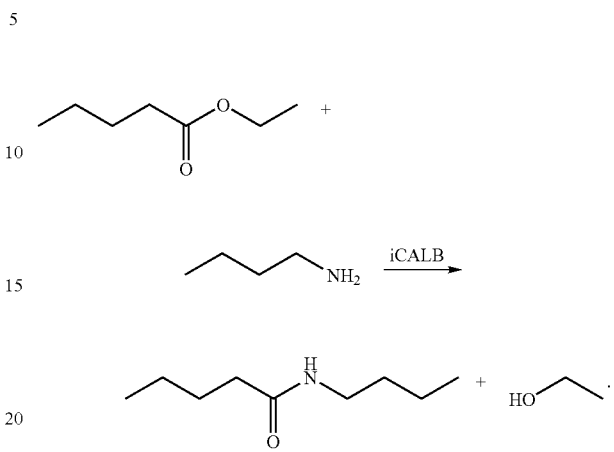

The reaction rates and final conversion (>90%) were similar in the DES's ChCl:Gly, ChCl:U or the organic solvent toluene. Aminolysis was slower in ChCl:Acet and gave only 39% conversion. In EAC:Gly aminolysis with ethylamine from the DES (4.5 M amine, 80% conversion) predominated over aminolysis with butylamine (11% conversion), likely due to proton exchange between butylamine with the ethylammonium cation. The relative amount of ethylamide formed is 7-fold less than the relative concentration of ethylamine. In contrast, the transesterification reactions above did not show competing aminolysis when using ethylammonium-chloride-containing DES's. A possible reason is that the ethylammonium ion remained protonated and unreactive because the transesterification reactions lacked a base.

The initial specific activity for aminolysis in DES's was also higher than in ionic liquids, Table 2. The aminolysis activity in the DES ChCl:Gly (52) was five times higher than in the ionic liquids BMIM[BF$_4$] or BMIM[Tf$_2$N] (9-11) and similar to the activity in the organic solvent toluene (46 µmol hr$^{-1}$ mg$^{-1}$).

DES's were also suitable as cosolvents for reactions in aqueous solution, where they surprisingly enhanced hydrolase-catalyzed reactions up to 20-fold. The rates of esterase-catalyzed hydrolysis of p-nitrophenyl acetate increased moderately upon addition of 10 vol % ChCl:Gly: three-fold increase for PLE and ROE and a 25% increase for PFE and CALB, see Example 4 and FIG. 2. The rate of epoxide hydrolase[11] catalyzed hydrolysis of styrene oxide increased dramatically: a 20-fold increase in conversion, see Table 3. The conversion was only 4.6% in buffer, but increased to 92% upon addition of 25 vol % ChCl:Gly, with no change in the enantioselectivity (E=16; another group has created a mutant with higher enantioselectivity, but it was not tested.[12]). Similar additions of organic solvents 10% or 25% DMSO or acetonitrile did not increase the conversion for epoxide hydrolase-catalyzed hydrolysis of styrene oxide, suggesting that the effect is not a simple increase in substrate solubility but is directly related to use of DES. Adding more than about 25 vol % DES decreased conversions. For example, the conversion of the EHAD1-catalyzed reaction decreased from 92% conversion in 25 vol % DES to 2% in 50 vol % DES. Similarly the rates of esterase-catalyzed hydrolysis of p-nitrophenyl acetate decreased in solutions containing more than 25 vol % DES.

TABLE 3

Conversion of styrene oxide by the enzyme EHAD1 in ChCl:Gly/buffer mixtures at 37° C. after 2 h.

| | Cosolvent Amount | | | | | |
|---|---|---|---|---|---|---|
| | 90%[a] | 75% | 50% | 25% | 10% | 0% |
| | | | (Buffer Amount) | | | |
| | (10%) | (25%) | (50%) | (75%) | (90%) | (100%) |
| Conversion with ChCl:Gly as cosolvent | 0% | 0% | 2.0% | 92% | 36% | 4.6% |
| Conversion with DMSO as cosolvent[b] | N.D. | N.D | N.D | 0.7% | 1.9% | 4.6% |
| Conversion with Acetonitrile as cosolvent | N.D | N.D | N.D | 0.1% | 0.7% | 4.6% |

[a] Cosolvent volume faction in solution containing 0.05 mg ml$^{-1}$ enzyme, 100 mM styrene oxide at 5 mM BES at pH 7.2 used as buffer.
[b] DMSO or acetonitrile added in place of DES.

The polarity of these DES's was higher than typical imidazolium-based ionic liquids according to the Reichardt's dye method, see Table 4 and Example 1, polarity estimation. The $E_T^N$ of the DES's ranged from 0.77 to 0.93 as compared to 0.53 to 0.75 for two imidazolium based ionic liquids.[13] The polarity of DES's containing the quaternary salt choline chloride was 0.08 to 0.09 units lower than the corresponding primary ethylammonium chloride DES's, which is consistent with the lower polarity of quartenary ammonium-based ionic liquids as compared to primary ammonium-based ionic liquids.[13]

TABLE 4

Solvent polarity according to color of dissolved Reichardt's dye.

| Solvent (Type) | ETN |
|---|---|
| Toluene (Organic) | 0.1014,[a] |
| DMSO (Organic) | 0.4414 |
| Acetonitrile (Organic) | 0.4614 |
| BMIM[Tf2N] (Ionic Liquid) | 0.6413 |
| BMIM[BF4] (Ionic Liquid) | 0.6813 |
| Methanol (Alcohol) | 0.7614 |
| ChCl:Acet (DES) | 0.77 |
| ChCl:EG (DES) | 0.80 |
| Glycerol (Glycerol) | 0.8114 |
| ChCl:Gly (DES) | 0.84 |
| ChCl:U (DES) | 0.84 |
| EAC:Acet (DES) | 0.85 |
| EAC:EG (DES) | 0.88 |
| EAC:Gly (DES) | 0.93 |

[a] Solvent polarity according to Reichardt's normalized polarity scale, where water has a polarity of 1.0 and trimethylsilane has a polarity of 0.0.

DES was also effective to support enzymatic catalysis as measured by initial reaction rates and enantioselectivity. The initial activity and enantioselectivity of iCALB toward ethyl valerate (100 mM) and 2-butanol (200 mM) was measured, see Table 5:

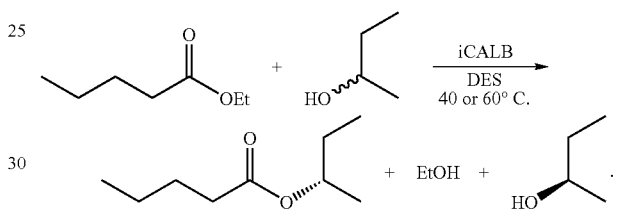

The conversion of ethyl valerate to 2-butyl valerate was measured after 15 minutes of reaction at 40° C. It was found that iCALB had a greater activity in each of the DES's tested than in the ionic liquid 1-butyl-3-methylimidazolium bis(trifluoromethanesulfonyl)imide (BMIM[TF$_2$N], 140 mU mg$^{-1}$), and had comparable activity compared to the organic solvent toluene (430 mU mg$^{-1}$). iCALB was most active in the DES's ChCl:U, ChCl:Gly, ChBr:Gly, and Et$_3$BzNCl:Gly, with initial activities of 990, 640, 580, and 450 mU mg$^{-1}$, respectively. DES's in which iCALB was less active than in toluene were AcChCl:Gly (410 mU mg$^{-1}$), Bu$_4$NCl:Gly (200 mU mg$^{-1}$), and ChCl:F (150 mU mg$^{-1}$). Transesterification in zinc chloride-based DES composed of 1 mol ZnCl2:3.5 mol urea (ZnCl2:U) was also tested (Table 5), with the procedure being identical to amine-based DES's for ethylvalerate transesterification with butanol, see also (47). Synthesis of this DES was the same as other DES's. After 15 minutes of reaction, the conversion of ethyl valerate was 19% with an enantioselectivity value of 7.2. The initial activity of iCALB in the DES was 260 mU mg-1.

TABLE 5

Initial Activity and Enantioselectivity of CALB-Catalyzed Transesterification of Ethyl Valerate and 2-Butanol in DES's.

| Solvent | Type of Solvent | Type of butanol | Initial Activity (mU mg$^{-1}$) | Enantioselectivity |
|---|---|---|---|---|
| Toluene | Organic | 1-butanol | 620 (36) | N/A |
| Toluene | Organic | 2-butanol | 430 | 9.9 |
| BMIM[Tf$_2$N] | RTIL | 1-butanol | 400 (36) | N/A |
| BMIM[Tf2N] | RTIL | 2-butanol | 140 | 3.1 |
| ChCl:Gly | DES | 1-butanol | 560 (36) | N/A |
| ChCl:Gly | DES | 2-butanol | 640 | 4.9 |
| ChCl:U | DES | 1-butanol | 340 (36) | N/A |

TABLE 5-continued

Initial Activity and Enantioselectivity of CALB-Catalyzed Transesterification of Ethyl Valerate and 2-Butanol in DES's.

| Solvent | Type of Solvent | Type of butanol | Initial Activity (mU mg$^{-1}$) | Enantioselectivity |
|---|---|---|---|---|
| ChCl:U | DES | 2-butanol | 990 | 3.6 |
| ChBr:Gly | DES | 2-butanol | 580 | 4.5 |
| Bu$_4$NCl:Gly | DES | 2-butanol | 200 | 2.8 |
| Et$_3$BzNCl:Gly | DES | 2-butanol | 450 | 5.2 |
| AcChClGly | DES | 2-butanol | 410 | 5.0 |
| ChCl:F | DES | 2-butanol | 150 | 4.4 |
| ChCl:D-Ara | DES | 2-butanol | 800 | 3.7 |
| ChCl:L-Ara | DES | 2-butanol | 830 | 3.2 |
| ChCl:Glc | DES | 2-butanol | 750 | 4.0 |
| ChCl:Xyl | DES | 2-butanol | 880 | 2.8 |
| ZnCl$_2$:U | DES | 2-butanol | 260 | 7.2 |

Conditions:
2-butanol - 15 min, 40° C. (or 30 min reaction, 60° C. for sugar-based DES's), 5 mg mL$^{-1}$ iCALB, 100 mM ethyl valerate, 200 mM 2-butanol.
1-butanol - 15 min, 60° C., 2.5 mg mL$^{-1}$ iCALB, 40 mM ethyl valerate, 400 mM 1-butanol. 1 U = 1 micromol product formed min$^{-1}$.

iCALB had reduced enantioselectivity in the DES's compared to the organic solvent toluene, but higher compared to the ionic liquid BMIM[Tf$_2$N]. While the enantioselectivity of the enzyme was 9.9 in toluene, it was half as much or less in the more active DES's. Compared to the enantioselectivity of iCALB in BMIM[Tf$_2$N] (3.1), the DES's were generally higher, with Bu$_4$NCl:Gly (2.8) as the exception. Et$_3$BzNCl:Gly gave the highest enantioselectivity of any DES (5.2), followed by AcChCl:Gly (5.0), ChCl:Gly (4.9), ChBr:Gly (4.5), ChCl:F (4.4), and ChCl:U (3.6).

Sugars can be effectively used in DES. iCALB had activity comparable to the organic solvent toluene in eutectic mixtures of sugars and choline chloride, see Table 5. Viscous mixtures of choline chloride and D-glucose (Glc), D-xylose (Xyl), and D- and L-arabinose (Ara) were synthesized and tested using the iCALB-catalyzed transesterification of ethyl valerate with 2-butanol. The reaction was carried out for 30 minutes at a temperature of 60° C. This temperature was used because the high viscosity of the sugar-based DES's inhibited flow at 40° C. Each DES had a higher initial activity than toluene (670 mU mg-1). The activity of iCALB in sugar-based DES's inversely followed a qualitative ranking of their viscosity: ChCl:Glc (750 mU mg-1) had the highest viscosity, ChCl:D-Ara (800 mU mg-1) and ChCl:L-Ara (830 mU mg-1) had lower apparent viscosities, and ChCl:Xyl (880 mU mg-1) had the lowest apparent viscosity. In all cases, the enantioselectivity of iCALB was reduced in the DES's compared to toluene (6.2). ChCl:Glc had the highest enantioselectivity of the DES's (4.0), while ChCl:D-Ara (3.7), ChCl:L-Ara (3.2), and ChCl:Xyl (2.8) were marginally lower. The DES's composed of opposite enantiomers of arabinose have very similar enantioselectivities, suggesting that the chiral center at which the arabinoses different does not likely significantly interact with either the substrate or enzyme.

DES were also effective in perhydrolysis enzymatic reactions. iCALB gave results in DES's comparable to an ionic liquid for the perhydrolysis of octanoic acid by hydrogen peroxide. Acetonitrile as solvents were generally more effective than the DES's tested. iCALB was used to catalyze the perhydrolysis of octanoic acid with hydrogen peroxide in ChCl:U, ChCl:Gly, acetonitrile, and 1-butyl-3-methylimidazolium tetrafluoroborate (BMIM[BF$_4$]) in a reaction similar to that used by Sheldon and coworkers (109):

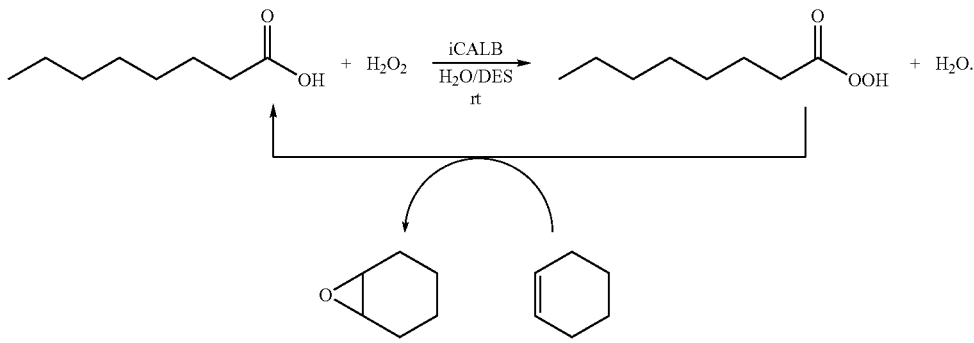

The water content after addition of the hydrogen peroxide solution was approximately 10 percent by volume. The reaction was monitored using the epoxidation oxidation of cyclohexene as a reporter reaction. Conversion of cyclohexene to expoxycyclohexane in ChCl:U (8%) and ChCl:Gly (22%) was comparable to BMIM[BF$_4$] (15%) after 24 h at room temperature, see Table 6. However, all of these alternative solvents gave much lower conversion than acetonitrile (79%), an excellent solvent for the reaction (109).

TABLE 6

Conversion of cyclohexene by peroctanoic acid formed by iCALB-catalyzed perhydrolysis

| Solvent | Type of solvent | Conversion (%) |
|---|---|---|
| MeCN | Organic | 79 |
| BMIM[BF4] | Ionic Liquid | 15 |
| ChCl:Gly | DES | 22 |
| ChCl:U | DES | 8 |

Conditions: 0.18 mL 50 wt % hydrogen peroxide added in six portions over 5 h to a mixture of 1.0 mL solvent, 0.3 mL cyclohexene, 60 µL octanoic acid, and 5 mg iCALB; stirred for 24 h total.

Alcohol dehydrogenase reactions may be performed in DES. This reaction was demonstrated with alcohol dehydrogenase activity in ChCl:Gly/water mixtures. A solution of 100 mM ethanol, 6 mM NAD+ in 0-50 vol % ChCl:Gly (1 choline chloride: 2 glycerol) was prepared in pH 9 100 mM CHES buffer. In a 96-well plate, 95 µl of solution was added per well, followed by 5 µl of 1 µg/ml alcohol dehydrogenase from baker's yeast. After addition of enzyme, the absorbance at 340 nm was monitored for 45 min at room temperature. No reaction was observed in the blank, and enzyme activity decreased with the addition of ChCl:Gly. The enzyme, however, was still active over the course of the run, see Table 7.

TABLE 7

Alcohol dehydrogenase activity in ChCl:Gly/water mixtures

| | Volume Percent ChCl:Gly | | | |
|---|---|---|---|---|
| | 0% | 10% | 25% | 50% |
| Activity (Abs/min) | 2.87 ± 0.26 | 2.09 ± 0.32 | 1.32 ± 0.45 | 0.75 ± 0.17 |

Values are average enzyme activity over entire reaction time with triplicate runs, error is one standard deviation.

DES was also effective to make polymers by enzymatic reactions. As an example, caprolactone was synthesized. 200 µl solvent was incubated with 100 µl ε-caprolactone, 3 mg immobilized *Candida antarctica* lipase B (iCALB) at 70° C. for 24 h in 2 ml vials. After incubation, the polymer was precipitated with 1.5 ml methanol and let stand 2 h at 4° C. Formation of white polymer precipitate was observed, see Table 8. No precipitate was observed in vials that contained no enzyme.

TABLE 8

Observed precipitates from enzymatic ring-opening of ε-caprolactone

| Solvent/ Condition | AcChCl: U | ChCl: S-Lac | ChCl: R-Lac | ChCl: U | ChCl: F | Bu$_4$NCl: U | Toluene |
|---|---|---|---|---|---|---|---|
| w/iCALB | ++ | ++ | + | ++ | + | + | ++ |
| no enzyme | – | – | – | – | – | – | – |

–: no polymer precipitation observed
+: trace amount of white precipitate formed
++: precipitate amount formed comparable to toluene TABLE 8-continued Observed precipitates from enzymatic ring-opening of ε-caprolactone

| Solvent/ Condition | AcChCl: U | ChCl: S-Lac | ChCl: R-Lac | ChCl: U | ChCl: F | Bu$_4$NCl: U | Toluene |
|---|---|---|---|---|---|---|---|

Abbreviations: AcChCl:U - 1 acetylcholine chloride:2 urea; ChCl:S-Lac - 1 choline chloride:2 S-lactamide; ChCl:R-Lac - 1 choline chloride:2 R-lactamide; ChCl:U - 1 choline chloride:2 urea; ChCl:F - 1 choline chloride:2 formamide; Bu$_4$NCl:U - 1 tetrabutylammonium chloride:2 urea All of these results show that a variety of enzymes are active in a variety of DES's. CALB is active in a wide variety of DES's. Strong hydrogen bond donors such as formamide, ammonium salts with more hydrophobic substituents, metal salts, and sugars were all tested as hydrogen bond donors. The DES's tested herein were comparable to organic solvents. Based this work any combination of nitrogen or metal salt and amide or polyol-based hydrogen bond donor could potentially be used as a solvent for enzymatic biotransformations, including transesterification or aminolysis, provided that i) the components can form a homogeneous mixture, ii) the hydrogen bonds between DES components are strong enough to reduce the reactivity and hydrogen bond basicity of the two components, and iii) the nitrogen or metal salt effectively has no potential for proton exchange with desired substrates.

Application of these criteria, specifically ii and iii, depend on the specific reaction involved. For instance, iCALB is stable in EAC:Gly, which is a homogeneous mixture and thus a DES. When EAC:Gly is the solvent for transesterification between ethyl valerate and butanol, the DES yields little or no side products from reaction with the substrates, and thus it can be considered suitable for the reaction. However, when the DES is a solvent for aminolysis of an ester, the free protons readily exchange with any free amine, resulting in significant amounts of ethyl amides instead of the desired amide (136), meaning that the DES is unsuitable due to violation of criterion iii. In the other extreme, iCALB is stable in both ChCl:Gly and ChCl:EG, but in the above case of transesterification, the ethylene glycol has a reactivity much higher than the glycerol and results in up to more than half of total conversion of ester. Despite an overall reduction in reactivity compared to free ethylene glycol due to hydrogen bonds, ChCl:EG was unsuitable for this transesterification because this reduction is simply insufficient.

The reduction of activity in DES, however, is often sufficient. Two potential side reactions of deep eutectic solvents in lipase-catalyzed reactions are shown below as (a0 and (b):

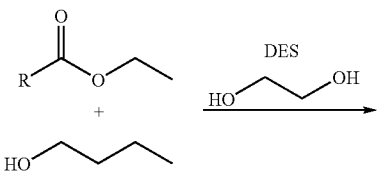

a)

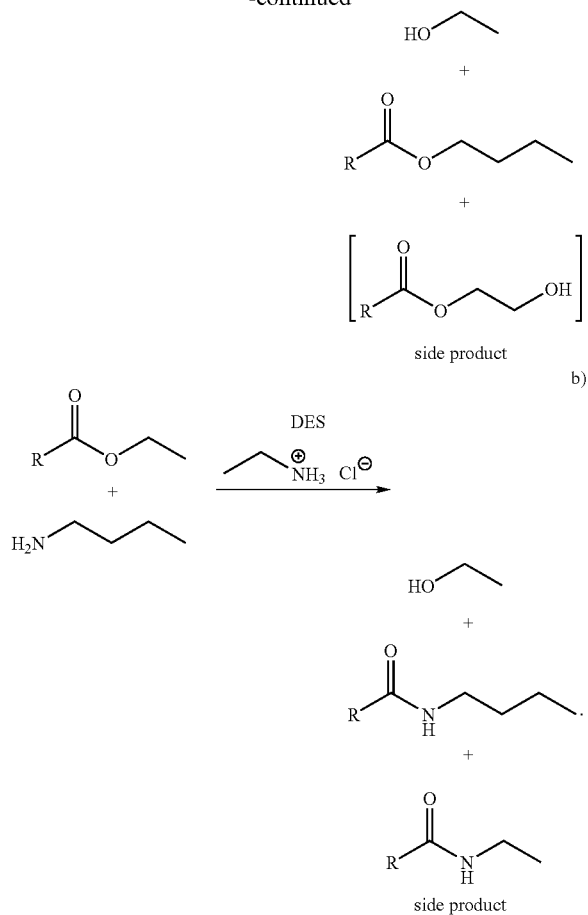

In (a), the ethylene glycol component in DES competes with 1-butanol in a CALB-catalyzed transesterification. The brackets indicate that gas chromatography did not detect this presumed side product. DES containing glycerol did not show this side reaction. In (b), the ethylamine component in DES competes with butylamine in a CALB-catalyzed aminolysis. This side reaction does not occur in transesterification reactions, presumably because the ethylamine remains protonated and unreactive.

In general, to satisfy criterion (i), components can be identified that form a suitable mixture, or the hole theory can be applied to design low-melting eutectics, with applications in designing deep eutectic solvents (123). To satisfy criterion (ii) hydrogen bond basicity can be estimated from measurement of the pKHB such that used by Taft (52-54), or using a computational method such as the one proposed by LaMarche and Platts (55). A large hydrogen bond basicity will likely denature proteins. Hydrogen bond strengths may also be estimated using techniques such as the one employed by Li and workers (56). To satisfy criterion (iii), quaternary ammonium salts (such as choline chloride) are unlikely to undergo proton exchange, making them generally suitable, and were successful for all reactions tested. Less substituted amines (such as ethylammonium chloride) are also generally suitable, except for aminolysis with non-quaternary amines because they present the possibility of proton donation to other amines, unless the DES is based on the same amine as the substrate, e.g. ethylammonium chloride DES's would likely be suited for aminolysis with ethylamine.

The term DES refers to compositions including an nitrogen or metal salt and a hydrogen bond donor that could form a eutectic point at some proportion, regardless of whether or not the proportions are actually at the eutectic point. An embodiment of a nitrogen salt is a salt with a positively charged nitrogen for a cation, including primary, secondary, tertiary, and quaternary nitrogen. An embodiment of a nitrogen salt is an ammonium salt, which is any salt that contains ammonium ($NH_4^+$) or a substituted ammonium. Another embodiment of a nitrogen salt is a nitrogen salt with a halide. An embodiment of a metal salt is a transition metal salt. Another embodiment of a metal salt is a metal salt with a halide. The hydrogen bond is any hydrogen bond donor that can form a eutectic point when mixed in appropriate proportions with the nitrogen or metal salt. Certain embodiments of a strong hydrogen bond donor may include hydroxyl, amide, amine, aldehyde, or carboxylic acid. Hydrogen bond donors thus include, for example, hydrogen halides, organic acids, urea, choline chloride, thiourea, molecules with a hydroxyl group, e.g., glycerols, diols, and propane diols.

Transition metals are the 40 chemical elements 21 to 30, 39 to 48, 71 to 80, and 103 to 112. The name transition comes from their position in the periodic table of elements. The halides are fluoride (F—), chloride (Cl—), bromide (Br—), iodide (I—) and astatide (At—).

Also, the embodiments that call for a DES may typically also be performed in an embodiment with the DES members being present in relatively balanced proportions, meaning a range from about 1:2 parts to about 2:1 parts of nitrogen or metal salt to strong hydrogen bond donor. Further, it is recognized that some contamination or other components may also be present in the DES so that a composition of DES with enzymes and/or reactants and/or products may or may not have an actual eutectic point, or such that the actual eutectic point is not as predicted based on a purified mixture. Accordingly, the embodiments that call for a DES may typically also be performed with an embodiment wherein the DES members are present in the composition at a concentration of more than about 25%, 50%, 75%, 85%, or 90% purity, with purity representing the weight percentage of the DES as compared to a total weight of the composition including any contaminants, additional components, or reactants and products; artisans will immediately appreciate that all the ranges and values within the explicitly stated ranges are contemplated, e.g., 30%.

Enzymatic reactions may be carried out in a pure DES or in a DES having a cosolvent present. One cosolvent is water, a term including buffered water. Table 3, for instance, describes how mixtures of DES and a cosolvent can be effective for enzymatic reactions. Accordingly, embodiments of compositions having a DES include DES concentrations from about 10% to about 90% DES vol/vol of the DES plus cosolvents; artisans will immediately appreciate that all the ranges and values within the explicitly stated ranges are contemplated; e.g., about 50% DES, about 25% DES, or from about 10% to about 50% DES.

DES may include, for example, choline chloride/acetamide (ChCl:Acet); choline chloride/ethylene glycol (ChCl:EG); choline chloride/glycerol (ChCl:Gly); choline chloride/urea (ChCl:U); choline chloride/malonic acid (ChCl:MA); ethylammonium chloride/acetamide; (EAC:Acet); ethylammonium chloride/ethylene glycol (EAC:EG); ethylammonium chloride/glycerol (EAC:Gly); choline bromide/glycerol (ChBr:Gly); terabutylammonium chloride/glycerol ($Bu_4$NCl:Gly); triethylbenzylammonium chloride/glycerol ($Et_3$BzNCl:Gly); acetylcholine chloride/glycerol (AcChCl:Gly); choline chloride/formamide (ChCl:F); choline chloride/arabinose (ChCl:Ara); choline chloride/glucose (ChCl: Glc); or choline chloride/xylose (ChCl:Xyl). The various hydrogen bond donors and nitrogen salts or metal salts may generally be mixed-and-matched as guided by the need to have a eutectic point. Many DES are about 1:1 to about 1:2 mixture of nitrogen salt: hydrogen bond donor or metal salt: hydrogen bond donor. Examples of hydrogen bond donors include carboxyls, hydroxyls, glycols, amides, and amines. Sugars are one category of DES components.

Many DES's are mixtures of amine chloride salts and urea, glycerol, or ethylene glycol. A wide range of organic acids is also available for ammonium chloride-based DES synthesis (121). DES's are also known that are composed of choline chloride, malonic acid, urea, and ethylene glycol dissolved of oxides of a variety of metals (122). Abbott and coworkers applied hole theory to design DES's containing ethylammonium chloride, as well as fluorinated hydrogen bond donors (123). Nkuku and LeSeur recently used DES's consisting of choline chloride and either malonic acid or trifluoroacetic acid to dissolve ferrocene. Electrochemical experiments and simulations showed that the DES's were shear-thinning non-Newtonian fluids (124).

Room temperature ionic liquids, e.g., for extractions or as solvents for chemical reactions and enzymatic reactions are known for a limited set of enzymes and reactions. A DES is not an ionic liquid. Ionic liquids are non-volatile, thermally stable, and have properties that can be varied to some extent based on the choice of cation and anion. However, room temperature ionic liquids have limitations including toxicity, high price, and a need for high purity, as even small amounts of water and halides can greatly affect physical properties. And a DES, unlike ionic liquids, includes an uncharged component, e.g., urea. Accordingly, one discovery is that DES are an attractive alternative to ionic liquids and organic solvents for enzyme-catalyzed reactions, despite the presence of halides and strong hydrogen bond donors. DES are generally available by simple synthesis, which involves only warming and stirring the components, e.g., for an hour or so, e.g., 1-3 hours; artisans will immediately appreciate that all the ranges and values within the explicitly stated ranges are contemplated. In contrast, synthesis of ionic liquids usually requires removal of salts, which can require multiple precipitations and chromatography to remove remaining traces. The components of DES's also are generally non-toxic; for example, glycerol and choline chloride are used as food additives. It is possible to use expensive or toxic components to make a DES, but the most common ones use inexpensive and non-toxic components.

Researchers have reported other applications of DES's as solvents. For example, Abbott and coworkers dissolved silver salts the DES's to dip coat copper surfaces with silver without the need for catalysts (125, 126). Electropolishing stainless steel can be accomplished with choline chloride-based DES's as alternatives to harsh solvents such as phosphoric and sulfuric acids (127, 128). Adding choline chloride to a biodiesel preparation removes the glycerol side product by forming a choline chloride-glycerol DES as a second phase (129). Ma and workers demonstrated $CO_2$ sequestration by an immobilized choline chloride-urea catalyzed reaction of an epoxide with $CO_2$ to selectively form cyclic carbonates without the need for co-solvents or additional catalysts (130). DES's containing $ZnCl_2$ can dissolve starch (131) and have conductivities similar to alkylpyridinium-based ionic liquids, making them suitable as inexpensive liquids for applications in batteries (132, 133). None of these processes, however, pointed to enzymatic applications.

One consideration for using DES's is viscosity of the reaction. In the case of the sugar-based DES's, the viscosity can be reduced with additives that enhance flowability. One option is to add a cosolvent, e.g., an aqueous solution, water, and/or an organic solvent. Another option is to add a hindered alcohol, e.g., a tertiary alcohol, e.g., tertiary butanol. Another option is to perform the reaction at an elevated temperature, e.g., about 40°-60° C.

Transesterification activity was demonstrated in a variety of DES's. For instance, Tables 1 and 2 show results of experiments using a lipase-catalyzed transesterification with four different enzymes in eight different DES's. Further transesterification was demonstrated in additional DES solvents and other substrates, with a comparison to organic and ionic liquid solvents, see for instance see Table 5. Transesterification is not the only reaction that enzymes can catalyze in the presence of DES.

Aminolysis activity was also demonstrated in a variety of DES's, for instance see Table 2 or FIG. 1. Further, because aminolysis results in the formation of amide bonds, which are the bonds that compose peptides, peptide synthesis is possible in these solvents. Accordingly some embodiments are directed to peptide synthesis in a DES. Natural or synthetic amino acids may be used. Moreover, polymerization in DES by formation of amide bonds is possible, as well as chemical reactions in DES that lead to formation of amide bonds.

Figure 2:
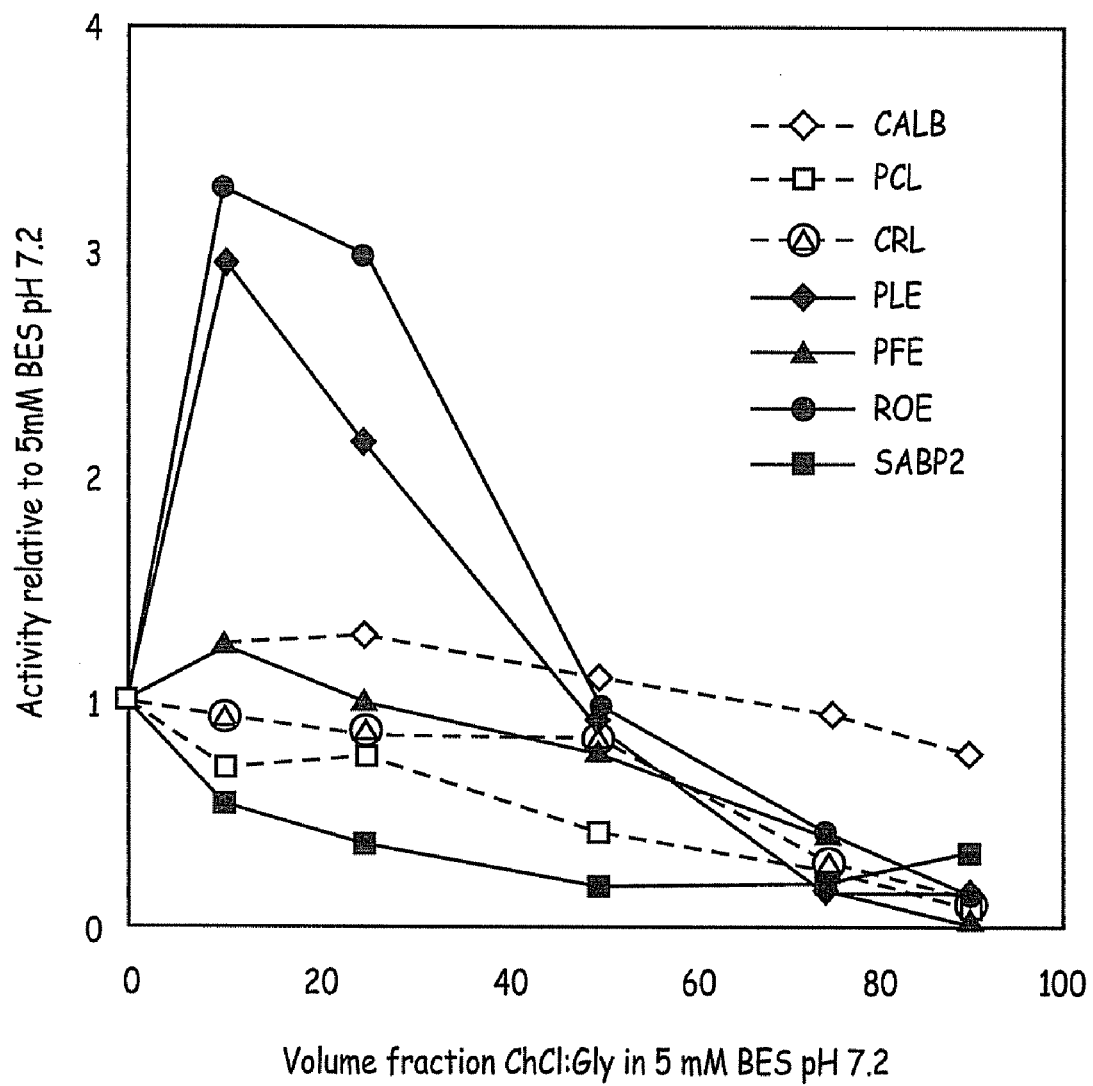
FIG. 2 is a demonstration of enzymatic hydrolytic activity in DES, showing a plot of p-nitrophenyl acetate (330 μM) by lipases and esterases (0.05 mg ml–1) at room temperature at different concentrations of ChCl:Gly in 5 mM BES buffer at pH 7.2. Activity is relative to the initial rate in the buffer only. Points are averages of quadruplicate runs and represent activity above the background reaction. Error was typically less than five percent.
Figure 3:
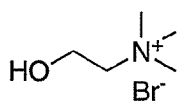
FIG. 3 depicts examples of DES components.
Figure 3:
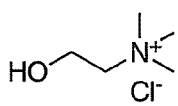
Figure 3:
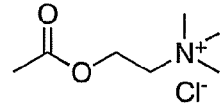
Figure 3:
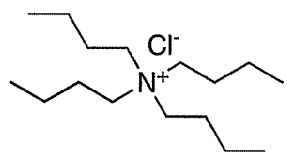
Figure 3:
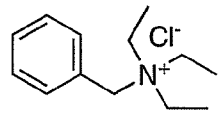
Figure 3:
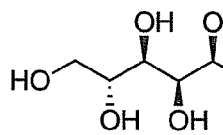
Figure 3:
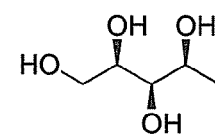
Figure 3:
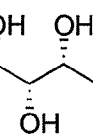
Figure 3:
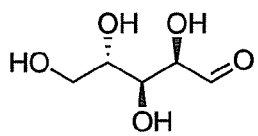
Figure 3:
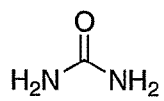
Figure 3:
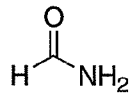
Figure 3:
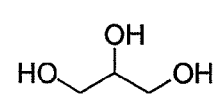

Hydrolysis activity was also demonstrated in a variety of DES's, for instance see FIG. 2 and Table 3. These reactions not only demonstrate that a variety of hydrolases are active in DES, they also show that DES's may be used as cosolvents for enzymatic reactions.

Perhydrolysis activity was also demonstrated in a variety of DES's, for instance see Table 6. This reaction underscores the breadth of possible reactions in DES. In the case of this reaction, hydrogen peroxide is not a natural substrate of *Candida antarctica* lipase B. The results show that promiscuous enzyme reactions are possible in DES. These results point to the success of embodiments directed to substrate/enzyme combinations already known in other solvents wherein DES is used as the solvent.

Further, the perhydrolysis assay was monitored indirectly by the chemical conversion of cyclohexene, which is immiscible with DES, to epoxycyclohexane by the enzymatic product. The fact that both the enzymatic and chemical reactions proceeded in a DES indicates that reactions in organic solvent/DES mixtures are possible and that enzymatic activity in DES is not limited solely to monophasic DES systems. These results support embodiments directed to any combination of solvents with DES's used for enzymatic reactions.

Alcohol dehydrogenase activity was also demonstrated in a variety of DES's, for instance see Table 7. These results show that activity in DES is not limited to the hydrolase class of enzymes. These results also support embodiments directed to dehydrogenases and their reactions in DES (enzymes that catalyze oxidation and reduction involving nicotinamide cofactors). Moreover, these results support embodiments directed to enzymes that catalyze oxidation and reduction reactions in DES. For instance, one such catalyzed reaction is the oxidation of ethanol to acetaldehyde, a prototypical oxidation reaction. Another example is the reduction of ketones or aldehydes to alcohols, or the reverse reaction. Another example is the oxidation of aldehydes to carboxylic acids, or the reverse reaction.

As is evident, many chemical reactions may be performed in a solution that comprises an enzyme and a DES, either substantially pure DES or DES and a cosolvent. The enzyme and enzymatic substrates may be present in effective concentrations and at ratios useful to make the intended product. An effective concentration excludes small concentrations of enzymes or precursors that are not useful to make the intended product in meaningful quantities. Accordingly, some embodiments have an enzymatic concentration of at least about 0.1, at least about 1, at least about 5, at least about 10, or at least about 20 mg enzyme per ml of solvent; artisans will immediately appreciate that all the ranges and values within the explicitly stated ranges are contemplated, e.g., from about 0.5 to about 10 mg/ml. Similarly, precursors may be present in certain embodiments in a concentration of at least about 1%, at least about 5%, at least about 10%, at least about 20%, or at least about 30% wt precursor/wt of solvent; artisans will immediately appreciate that all the ranges and values within the explicitly stated ranges are contemplated, e.g., from about 5% to about 25%. Embodiments of reactions include hydrolase or oxido-reductase catalyzed reactions, e.g., hydrolase (E.C. 3) or oxido-reductase (E.C. 1)-catalyzed reactions.

DES was also effective to make polymers by enzymatic reactions, for instance see Table 8. A polymer refers to a molecule with two or more repeating groups, with the repeating group being referred to as a "mer". Polymers may be made that are quite low in molecular weight or that have a molecular weight of at least about 1000, at least about 2,000, at least about 5,000, or at least about 10,000.

A composition that is, or comprises, a DES may be used. Various schemes for enzymatic polymerization may be adapted to DES as described herein, e.g., as in US Pub. No. 20040019178, U.S. Pat. Nos. 4,791,168, 4,794,147, 5,147, 791, 5,270,421, 5,474,915, 5,631,343, 5,981,240, or 6,677, 427, which are hereby incorporated herein by reference, with the instant specification controlling in case of a conflict. Accordingly, an embodiment of polymerization is a method for enzymatic condensation polymerization comprising combining a preselected quantity of an enzyme in a DES or a solution comprising a DES with at least one polymeric precursor. A reaction vessel loaded with precursors and an enzyme may be maintained as needed to produce the polymer, e.g., by addition or condensation. The temperature may be adjusted and maintained as needed, e.g., heated in the case of DES with a sugar component.

A polymerization embodiment is the formation of a polyester, with a ring-opening process with a chemical comprising a ring structure as the precursor, e.g., a lactone selected from the group consisting of lactones with 4 to 16 membered rings, e.g., epsilon-caprolactone, lactide, dioxanone or glycolide. In another embodiment the precursors comprise a diacid and at least one compound selected from the group consisting of diols and polyols, e.g., to form a polyester. Embodiments of diols may be, for instance, diols that contain from 2 to 32 carbon atoms, or diols including a structure of HO—R—OH, wherein R is a linear chemical structure. Embodiments of diols include, e.g., ethylene glycol, 1,3-propane diol, 1,4-butanediol, 1,5-pentanediol, 1,6-hexanediol, 1,8-octanediol, or 1,12-dodecanediol. Embodiments of polyols include, polyols having at least three hydroxyl groups of which at least two are primary or highly reactive secondary hydroxyl groups, or glycerol, erythritol, pentaerythritol, xylitol, ribitol, sorbitol, 1,2,6 hexane triol, 1,2,4-butanetriol, maltose, sucrose, or lactose. Embodiments of diacids may be, e.g., acids with a HOOC—R—COOH structure, with R being a linear chemical structure, e.g., a aliphatic dicarboxylic acid.

A polymerization embodiment is the formation of a polyamide. The polyamide may be a polyamino acid, e.g., a protein. Amino acids may be reacted with an enzyme to form amide bonds. The amino acid side groups may be protected as needed to prevent unwanted side reactions.

Or the polyamide may be a synthetic polymer. One embodiment for polyamide polymerization is enzymatic reaction of one or more precursors that comprise a diacid, a polyacid, a diester, a polyester, a diamine, or a polyamine. Embodiments of a diester include, e.g., diester comprises dialkyl malonate, dialkyl fumarate, dialkyl maleate, dialkyl adipate, dialkyl glutarate, dialkyl succinate, dialkyl oxalate, dialkyl phenylmalonate, or a mixture thereof. Embodiments of a polyamine are, e.g., polyalkylpolyamine, polyalkenylpolyamine, polyaralkylenepolyamine, polyalkarylenepolyamine, polyarylenepolyamine, diethylene triamine (DETA), triethylene glycol diamine, ethylenediamine (EDA), bishexamethylenediamine (BHMT), hexamethylenediamine (HMDA), triethylenetetramine (TETA), tetraethylenepentamine (TEPA), dipropylenetriamine (DPTA), tripropylenetetramine (TPTA), tetrapropylenepentamine (TPPA), N-methyl-bis-(aminopropyl)amine (MBAPA), spermine, spermidine, 1-phenyl-2,4-pentane diamine, 2-phenyl-1,3-propanediamine, phenylene diamine or mixtures thereof. Diacids may include, e.g., one or more carboxylic acids, e.g., an aliphatic diacid.

Example 1

A. General Reagents and enzymes were purchased from Sigma-Aldrich, except where described below. Ionic liquids were purchased from Solvent Innovation (Cologne, Germany). SABP2 was expressed and purified according to Kumar, et al[1]. PFE was expressed and purified according to Cheeseman, et al[2]. In all cases, blank reactions were run alongside the enzymatic reactions and gave negligible conversion, with the exception of ChCl:MA, as shown in Table 1, above.

B. DES Synthesis Synthesis of deep eutectic solvents: nitrogen salt (0.05 mol) and hydrogen bond donor (0.1 mol for choline chloride mixtures, 0.075 mol for ethylammonium chloride mixtures) were added to a 20-ml vial and heated at 80° C. until a clear, homogenous liquid formed, typically one hour. Or DES's were prepared according to Abbott and coworkers (119). For amide and glycerol-based DES's, nitrogen salt (0.05 mol) and hydrogen bond donor (0.1 mol) were combined in a 20-mL vial and stirred at 60 to 80° C. until a homogeneous liquid formed, typically one hour. For sugar-based DES's, nitrogen salt (0.05 mol) and sugar (0.05 mol) were combined as above, and stirred at 100° C. until a homogeneous liquid formed, typically several hours. The sugar-based DES's are very viscous, so they were warmed to 60° C. before use. Metal salt DES were synthesized in the same manner.

C. Gas chromatography The detector and injector temperatures were 275° C. and 250° C., respectively. Analysis of transesterification and aminolysis products was performed using a 30 m HP-5 column (J&W Scientific, Folsom, Calif.) with 0.32 mm inner diameter and 0.25 μm film size. The initial column temperature of 60° C. was held for 6 min, then increased to 165° C. at 15° C. min$^{-1}$, then further increased to 200° C. at 25° C. min$^{-1}$ and held at 200° C. for 5 min. Products of styrene oxide hydrolysis were analyzed on a 25 m CP 7502 column (Varian) with 0.25 mm inner diameter and 0.25 μm film size. The initial column temperature of 50° C. was held for 5 min, then increased to 200° C. at 10° C. min$^{-1}$ held at 200° C. for 5 min.

D. Transesterification reaction Enzyme (2.0 mg solid; note that iCALB contains only ~10 wt % protein) was suspended in solvent (0.2 ml) in a glass vial. Ethyl valerate (40 mM) and butanol (400 mM) were added to the suspension and the resulting mixture was stirred at 60° C. for up to 24 h. The reaction products were extracted with toluene (1.0 ml) and analyzed by GC. Or, see Table 5, Immobilized CALB (iCALB, 1.0 mg of immobilized enzyme preparation) was suspended in solvent (0.2 mL) in a glass vial. Ethyl valerate (3.0 µL, 100 mM) and 2-butanol (3.7 µL, 200 mM) were added to the suspension and the resulting mixture was stirred at 40° C. For sugar-based DES's, the reaction temperature was 60° C. The reaction products were extracted with toluene (1.0 mL) and analyzed on a CP 7502 column (Varian, 25 m×0.25 mm inner diameter and 0.25 µm film thickness). The initial column temperature of 50° C. was held for 8 min, then increased to 200° C. at 10° C. $\min^{-1}$ held at 200° C. for 5 min.

E. Aminolysis reaction Enzyme (2.0 mg solid; note that iCALB contains only ~10 wt % protein) was suspended in solvent (0.2 ml) in a glass vial. Ethyl valerate (100 mM) and butylamine (110 mM) were added to the suspension and the resulting mixture was stirred at 60° C. for up to 24 h. The reaction products were extracted with toluene (1.0 ml) and analyzed by GC.

F. Hydrolysis of p-nitrophenyl acetate A 0.5 mg protein $ml^{-1}$ solution in 5 mM BES at pH 7.2 (10 µl) was added to a p-nitrophenyl acetate solution (30 mM, 90 µl), acetonitrile (7.4% v/v), and a mixture of 5 mM BES at pH 7.2 and ChCl:Gly. The final DES volume fraction was 0, 0.1, 0.25, 0.5, 0.75, or 0.9. The absorbance was monitored at 404 nm at 6-second intervals with a microplate reader (SPECTRAMAX 384 Plus, Molecular Devices) at room temperature for up to 40 minutes.

G. Hydrolysis of styrene oxide A mixture (0.2 ml) of styrene oxide (100 mM), 5 mM BES at pH 7.2, and sufficient ChCl:Gly to give DES volume fractions of 0, 0.1, 0.25, 0.5, 0.75, and 0.9 was prepared. A 10 mg $ml^{-1}$ protein solution in 5 mM BES at pH 7.2 (2 µl) was added to the suspension to start the reaction. The reaction mixture was incubated at 37° C. for 2 h, after which the mixture was extracted with ethyl acetate (1.0 ml) and analyzed by GC.

H. Polarity estimation Reichardt's dye (2,6-diphenyl-4-(2,4,6-triphenylpyridinio)phenolate, 0.4 mg) was dissolved in DES (0.5 ml). An aliquot was transferred to a 96-well microplate. The wavelength of the absorption maximum of the long-wavelength transition ($\lambda_{max}$) was measured at room temperature using a Spectra Max 384 Plus. Normalized polarity values ($E_T^N$) were calculated from the equation[3]

$$E_T^N = \frac{E_T(solvent) - E_T(TMS)}{E_T(water) - E_T(TMS)} = \frac{E_T(solvent) - 30.7}{32.4}$$

where $E_T$(solvent) is the energy (kcal $mol^{-1}$) of the maximum of the long wavelength transition and is given by $$E_T(solvent) (kcalmol^{-1}) = \frac{28591}{\lambda_{max} (nm)}.$$

Example 2

Stability of CALB in ChCl:U

CALB (2 mg $ml^{-1}$) was preincubated in either 10 M urea or 5 M choline chloride in deionized water (0.3 ml) for 30, 60, and 90 min at 60° C. After the allotted time, the hydrolysis activity of p-nitrophenyl acetate was examined and compared to a mixture with no preincubation. After 90 min in 10 M urea, CALB lost 70% of its initial activity, and the first-order rate constant for the degradation had a value of $7\times10^{-3}$ $min^{-1}$. For 5 M choline chloride, the value of the degradation rate constant was $4\times10^{-3}$ $min^{-1}$, corresponding to an activity loss of 25% after 90 min. CALB (0.2 mg $ml^-$) in ChCl:U (0.3 ml) was then preincubated for up to 90 min. The transesterification activity of the enzyme was then examined, and found to be changed <1% in activity over the course of the experiment, corresponding to a rate constant of less than $2\times10^{-4}$ $min^{-1}$. Based on these results, CALB is at least 20- and 35-fold more stable in ChCl:U than in 5 M choline chloride or 10 M urea, respectively. The enzyme experienced <1% activity loss in 90 min at 60° C. compared with 25% loss in the choline chloride solution and 70% loss in the urea solution.

In order to determine long term stability in a DES, free iCALB was incubated in both toluene and ChCl:Gly for 18 h at 60° C. The initial rate of transesterification of ethyl valerate to butyl valerate was then tested and compared to the rate prior to incubation. There was a 12% loss of activity in toluene and 5% loss of activity in ChCl:Gly, which indicates that, under relatively harsh conditions, the enzyme iCALB is at least twice as stable in the deep eutectic solvent than in the common organic solvent toluene.

Example 3

Transesterification in Glycerol-Containing DES: ChCl:Gly

An iCALB-catalyzed transesterification of pure glycerol with ethyl valerate in tert-butanol (glycerol and its esters of valeric acid are poorly soluble in toluene.) showed a peak in the GC trace consistent with glyceryl monoester of valeric acid. A similar reaction with 1-butanol as the nucleophile and toluene as the solvent showed the expected 1-butyl valerate. The same reaction in ChCl:Gly after extraction with tert-butanol (1.0 ml) instead of toluene, showed 95% conversion to 1-butyl valerate and <0.5% conversion to the glyceryl monoester of valeric acid.

Example 4

Hydrolysis of P-Nitrophenyl Acetate by Lipases and Esterases

Hydrolysis assays were run in 0% to 90% ChCl:Gly with three lipases and four esterases. Four enzymes showed higher activity in 10% DES as compared to buffer only: CALB (125%), *Psuedomonas fluorescens* esterase (PFE) (125%), PLE (pig liver esterase) (284%), and *Rhizopus oryzae* esterase (ROE) (328%). At 25% DES, three enzymes still had higher activity as compared to buffer only: CALB (130%), PLE (215%), and ROE (299%). At 50%, only CALB retained higher activity as compared to buffer only: 112%. At 25% to 90% DES, all enzymes showed lower activity as compared to buffer only. At 90% DES PLE and Amano PS lyophilized *Burkholderia* (formerly *Pseudomonas*) *cepacia* lipase) (PCL) showed the lowest activity as compared to buffer only: 1% and 6%, respectively. Hydrolytic activity of p-nitrophenyl acetate (330 µM) by lipases and esterases (0.05 mg $ml^-$) was measured at room temperature at different concentrations of ChCl:Gly in 5 mM BES buffer at pH 7.2. Activity was relative to the initial rate in the buffer only. Points were averages of quadruplicate runs and represent activity above the background reaction. Error was typically less than five percent.

See D. Kumar and D. F. Klessig, 2003, *Proc. Nat. Acad. Sci. USA*, 100, 16101; J. D. Cheeseman, A. Tocilj, S. Park, J. D. Schrag and R. J. Kazlauskas, 2004, *Acta Cryst.*, D60, 1237; C. Reichardt, 1994, *Chem. Rev.*, 94, 2319.

Example 5

Perhydrolysis

Immobilized CALB (iCALB, 5.0 mg of immobilized enzyme preparation) was suspended in solvent (1.0 mL) in a glass vial. Cyclohexene (0.3 mL) and octanoic acid (60 μL) were added to the suspension and the resulting mixture was stirred at room temperature. Hydrogen peroxide (0.18 mL of a 50 wt % solution in water, 1.1 equiv total) was added in six portions over the first five hours of reaction. After 24 h, the reaction products were extracted with toluene (1.0 mL) and analyzed by GC on an HP-5 column (J&W Scientific, Folsom, Calif., 30 m×0.32 mm inner diameter and 0.25 μm film thickness). The initial column temperature of 60° C. was held for 6 min, then increased to 165° C. at 15° C. $min^{-1}$, then further increased to 200° C. at 25° C. $min^{-1}$ and held at 200° C. for 5 min.

Many embodiments have been described herein with various features. In general, the various features may be mixed-and-matched to provide combinations that are not explicitly set forth herein, as guided by the specification and the need to make functional embodiments.

REFERENCES

References are hereby incorporated herein by reference; in the case of conflict, the instant specification controls.

1 T. Welton, *Chem. Rev.*, 1999, 99, 2071; P. Wasserscheid and W. Keim, *Angew. Chem. Int. Ed.*, 2000, 39, 3772; P. Wasserscheid and T. Welton, *Ionic Liquids in Synthesis*, 2003, Wiley-VCH.
2 J. G. Huddleston, A. E. Visser, R. P. Swatlowski, W. M. Reichert, S. T. Griffin and R. D. Rogers, *Ind. Eng. Chem. Res.*, 29, 3596; H. Zhao, S. Xia and P. Ma, *J. Chem. Technol. Biotechnol.*, 2005, 80, 1089.
3 H. Zhao and S. V. Moltrova, *Aldrichim. Acta*, 2002, 35, 75; C. M. Gordon, *Appl. Catal. A. Gen.*, 2001, 222, 101; N. Jain, A. Kumar, S. Chauhan and S. M. S. Chauhan, *Tetrahedron*, 2005, 61, 1015.
4 R. M. Lau, F. van Rantwijk, K. R. Seddon, and R. A. Sheldon, *Org. Lett.*, 2000, 2, 4189; P. Lozano, T. De Diego, D. Carrié, M. Vaultier and J. L. Iborra, *Biotechnol. Lett.*, 2001, 23, 1529; U. Kragl, M. Eckstein and N. Kaftzik, *Curr. Opin. Biotechnol.*, 2002, 13, 565; R. A. Sheldon, R. M. Lau, M. J. Sorgedrager, F. van Rantwijk and K. R. Seddon, *Green Chem.*, 2002, 4, 147; S. Park and R. J. Kazlauskas, *Curr. Opin. Biotechnol.*, 2003, 14, 432.
5 B. Jastorff, R. Störmann, J. Ranke, K. Mölter, F. Stock, B. Oberheitmann, W. Hoffmann, J. Hoffmann, M. Nüchter, B. Ondruschka and J. Filser, *Green Chem.*, 2003, 5, 136; J. Ranke, K. Mölter, F. Stock, U. Bottin-Weber, J. Poczobutt, J. Hoffmann, B. Ondruschka, J. Filser and B. Jastorff, *Ecotoxicol. Environ. Saf.*, 2004, 58, 396; S. Stolte, J. Arning, U. Bottin-Weber, M. Matzke, F. Stock, K. Thiele, M. Uerdingen, U. Welz-Biermann, B. Jastorff and J. Ranke, *Green Chem.* 2006, 8, 621.
6 K. R. Seddon, A. Stark and M. Torres, *Pure Appl. Chem.* 2000, 72, 2275; A. K. Burrell, R. E. Del Sesto, S. N. Baker, T. M. McCleskey and G. A. Baker, *Green Chem.*, 2007, 9, 449.
7 A. P. Abbott, G. Capper, D. L. Davies, R. K. Rasheed, and V. Tambyrajah, *Chem. Commun.*, 2003, 70; A. P. Abbott, D. Boothby G. Capper, D. L. Davies, and R. K. Rasheed, *J. Am. Chem. Soc.*, 2004, 126, 9142; A. P. Abbott, G. Capper, D. L. Davies, K. J. McKenzie and S. U. Obi, *J. Chem. Engr. Data*, 2006, 51, 1280; A. P. Abbott, G. Capper, K. J. McKenzie, and K. S. Ryder, *J. Electroanal. Chem.*, 2007, 599, 288; A. P. Abbott, P. M. Cullis, M. J. Gibson, R. C. Harris and E. Raven, *Green Chem.*, 2007, 9, 868.
8 S. H. Lee, S. H. Ha, S. B. Lee and Y. M. Koo, *Biotechnol. Lett.*, 2006, 28, 1335.
9 J. T. Gorke, K. Okrasa, A. Louwagie, R. J. Kazlauskas, and F. Srienc, *J. Biotechnol.*, 2007, in press.
10 S. Park and R. J. Kazlauskas, R. J., *J. Org. Chem.*, 2001, 66, 8395.
11 J. H. L. Spelberg, R. Rink, R. M. Kellogg, D. B. Janssen, *Tetrahedron Asymm.*, 1998, 9, 459; R. Rink and D. B. Janssen, *Biochemistry*, 1998, 37, 18119.
12 R. Lingun, L. Cao, W. Chen, K. F. Reardon, T. K. Wood, *Appl. Env. Microbiol.*, 2005, 71, 3995; R. Rink, J. H. L. Spelberg, D. B. Janssen, R. Furstoss, *Tetrahedron*, 2001, 57, 2775.
13 C. Reichardt, *Green Chem.*, 2005, 7, 339.
14 C. Reichardt, *Chem. Rev.*, 1994, 94, 2319.
15 Welton, T. *Chem. Rev.* 1999, 99, 207.
16 Wasserscheid, P.; Keim, W. *Angew. Chem., Int. Ed.* 2000, 39, 3772.
17 Wasserscheid, P.; Welton, T. *Ionic Liquids in Synthesis*; Wiley-VCH: Weinheim, 2003.
18 Huddleston, J. G.; Visser, A. E.; Swatlowski, R. P.; Reichert, W. M.; Griffin S. T.; Rogers, R. D. *Ind. Eng. Chem. Res.* 2000, 29, 3596.
19 Zhao, H.; Xia S.; Ma, P. J. *Chem. Technol. Biotechnol.* 2005, 80, 1089.
20 Zhao, H.; Moltrova, S. V. *Aldrichimica Acta* 2002, 35, 75.
21 Gordon, C. M. *Appl. Catal. A* 2001, 222, 101.
22 Jain, N.; Kumar, A.; Chauhan, S.; Chauhan, S. M. S. *Tetrahedron* 2005, 61, 1015.
23 Lau, R. M.; van Rantwijk, F.; Seddon K. R.; Sheldon, R. A. *Org. Lett.* 2000, 2, 4189.
24 Lozano, P.; De Diego, T.; Carrie, D.; Vaultier M.; Iborra, J. L. *Biotechnol. Lett.* 2001, 23, 1529.
25 Kragl, U.; Eckstein, M.; Kaftzik, N. *Curr. Opin. Biotechnol.* 2002, 13, 565.
26 Sheldon, R. A.; Lau, R. M.; Sorgedrager, M. J.; van Rantwijk, F.; Seddon, K. R. *Green Chem.* 2002, 4, 147.
27 Park S.; Kazlauskas, R. J. *Curr. Opin. Biotechnol.* 2003, 14, 432.
28 Jastorff, B.; Störmann, R.; Ranke, J.; Mölter, K.; Stock, F.; Oberheitmann, B.; Hoffmann, W.; Hoffmann, J.; Nüchter, M.; Ondruschka, B. and Filser, J. *Green Chem.* 2003, 5, 136.
29 Ranke, J.; Mölter, K.; Stock, F.; Bottin-Weber, U.; Poczobutt, J.; Hoffmann, J; Ondruschka, B.; Filser J.; Jastorff, B. *Ecotoxicol. Environ. Safety* 2004, 58, 396.
30 Stolte, S.; Arning, J.; Bottin-Weber, U.; Matzke, M.; Stock, F.; Thiele, K.; Uerdingen, M.; Welz-Biermann, U.; Jastorff, B.; Ranke, J. *Green Chem.* 2006, 8, 621.
31 Seddon, K. R.; Stark, A.; Torres, M. *Pure Appl. Chem.* 2000, 72, 2275.
32 Burrell, A. K.; Del Sesto, R. E.; Baker, S. N.; McCleskey, T. M.; Baker, G. A. *Green Chem.*, 2007, 9, 449.
33 Abbott, A. P.; Capper, G.; Davies, D. L.; Rasheed, R. K.; Tambyrajah, V. *Chem. Commun.* 2003, 70-71.
34 Abbott, A. P.; Harris, R. C.; Ryder, K. S. *J. Phys. Chem. B* 2007, 111, 4910.

35. Abbott, A. P.; Capper, G.; Davies, D. L.; McKenzie, K. J.; Obi, S. U. *J. Chem. Eng. Data* 2006, 51, 1280.
36. Abbott, A. P.; Boothby, D.; Capper, G.; Davies, D. L.; Rasheed, R. K. *J. Am. Chem. Soc.* 2004, 126, 9143.
37. Abbott, A. P.; Capper, G.; Gray, S. *Chem. Phys. Chem.* 2006, 7, 803.
38. Nkuku, C. A.; LeSuer, R. J. *J. Phys. Chem. B* 2007, 111, 13271.
39. Abbott, A. P.; Griffith, J.; Nandhra, S.; O'Connor, C.; Postlethwaite, S.; Ryder, K. S.; Smith, E. L. *Surf. Coat. Technol.* 2008, 202, 2033.
40. Abbott, A. P.; Nandhra, S.; Postlethwaite, S.; Smith, E. L.; Ryder, K. S. *Phys. Chem. Chem. Phys.* 2007, 9, 3735.
41. Abbott, A. P.; Capper, G.; Swain, B. G.; Wheeler, D. A. *Transact. Inst. Metal Finish.* 2005, 83, 51.
42. Abbott, A. P.; Capper, G.; McKenzie, K. J.; Glidle, A.; Ryder, K. S. *Phys. Chem. Chem. Phys.* 2006, 8, 4214.
43. Abbott, A. P.; Cullis, P. M.; Gibson, M. J.; Harris, R. C.; Raven, E. *Green Chem.* 2007, 9, 868.
44. Zhu, A.; Jiang, T.; Han, B.; Zhang, J.; Xie, Y.; Ma, X. *Green Chem.* 2007, 9, 169.
45. Biswas, A.; Shogren, R. L.; Stevenson, D. G.; Willett, J. L.; Bhowmik, P. K. *Carbohyd. Polym.* 2006, 66, 546.
46. Abbott, A. P.; Capper, G.; Davies, D. L.; Munro, H. L.; Rasheed, R. K.; Tambyrajah, V. *Chem. Commun.*, 2001, 2010.
47. Abbott, A. P.; Barron, J. C.; Ryder, K. S.; Wilson, D. *Chem. Eur. J.* 2007, 13, 6495.
48. Parnham, E. R.; Drylie, E. A.; Wheatley, P. S.; Slawin, A. M. Z.; Morris, R. E. *Angew. Chem. Int. Ed.* 2006, 45, 4962.
49. Abbott, A. P.; Bell, T. J.; Handa, S.; Stoddart, B. *Green Chem.* 2006, 8, 784.
50. Gorke, J. T.; Srienc, F.; Kazlauskas, R. J. *Chem. Commun.* 2008, 10, 1235.
51. Trodler, P.; Pleiss, J. *BMC Structural Biology* 2008, 8, 9.
52. Gurka, D.; Taft, R. W. *J. Am. Chem. Soc.* 1969, 91, 4794.
53. Taft, R. W.; Gurka, D.; Joris, L.; von R. Schleyer, P.; Rashkys J. W. *J. Am. Chem. Soc.* 1969, 91, 4801.
54. Joris, L.; Mitsky, J.; Taft, R. W.; *J. Am. Chem. Soc.* 1972, 94, 3438.
55. Lamarche, O. and Platts, J. A. *Chem. Eur. J.* 2002, 8, 457.
56. Dong, H.; Hua, W.; and Li, S. *J. Phys. Chem. A* 2007, 111, 2941.

The invention claimed is:

1. A composition for enzymatic reaction comprising a deep eutectic solvent and an enzyme wherein the deep eutectic solvent comprises a first component taken from the group consisting of choline chloride, ethylammonium chloride, choline bromide glycerol, terabutylammonium chloride, triethylbenzylammonium chloride, zinc chloride, and acetylcholine chloride, and a second component taken from the group consisting of acetamide ethylene glycol, glycerol, urea, malonic acid, formamide, arabinose, glucose, and xylose.

2. The composition of claim 1 further comprising a substrate for the enzyme.

3. The composition of claim 1 wherein the substrate comprises a monomer or a macromer and catalysis by the enzyme produces a polymer of the monomer or macromer.

4. The composition of claim 1 wherein the enzyme is chosen from the group consisting of enzymes that catalyze transesterification, aminolysis, hydrolysis, perhydrolysis, alcohol dehydrogenation, oxidation-reduction, and dehydrogenation.

5. The composition of claim 1 wherein the enzyme is a member of the group consisting of transesterase, hydrolase, lipase, amidase, and dehydrogenase.

6. The composition of claim 1 wherein the composition comprises between about 10% and about 75% volume/volume of the deep eutectic solvent.

7. The composition of claim 1 wherein the first component comprises choline chloride.

8. The composition of claim 7 wherein the second component comprises urea.

9. The composition of claim 8 wherein the enzyme comprises *Candida Antarctica* lipase B.

10. The composition of claim 9 wherein the substrate comprises ethyl valerate.

11. The composition of claim 1 wherein the deep eutectic solvent comprises the choline chloride.

12. The composition of claim 1 wherein the deep eutectic solvent comprises the ethylammonium chloride.

13. The composition of claim 1 wherein the deep eutectic solvent comprises the choline bromide glycerol.

14. The composition of claim 1 wherein the deep eutectic solvent comprises the terabutylammonium chloride.

15. The composition of claim 1 wherein the deep eutectic solvent comprises the triethylbenzylammonium chloride.

16. The composition of claim 1 wherein the deep eutectic solvent comprises the zinc chloride.

17. The composition of claim 1 wherein the deep eutectic solvent comprises the acetylcholine chloride.

18. The composition of claim 1 wherein the deep eutectic solvent comprises the acetamide ethylene glycol.

19. The composition of claim 1 wherein the deep eutectic solvent comprises the glycerol.

20. The composition of claim 1 wherein the deep eutectic solvent comprises the urea.

21. The composition of claim 1 wherein the deep eutectic solvent comprises the malonic acid.

22. The composition of claim 1 wherein the deep eutectic solvent comprises the formamide.

23. The composition of claim 1 wherein the deep eutectic solvent comprises the arabinose.

24. The composition of claim 1 wherein the deep eutectic solvent comprises the glucose.

25. The composition of claim 1 wherein the deep eutectic solvent comprises the xylose.

* * * * *